United States Patent
Yukawa et al.

[11] Patent Number: 6,153,733
[45] Date of Patent: Nov. 28, 2000

[54] (DISULFONYL DIAZOMETHANE COMPOUNDS)

[75] Inventors: Hiroto Yukawa, Yokohama; Waki Ohkubo; Kouki Tamura, both of Kanagawa-ken; Toshiharu Shimamaki, Neyagawa; Kei Mori, Hirakata, all of Japan

[73] Assignees: Tokyo Ohka Kogyo Co., Ltd., Kanagawa-ken; Daito Chemix Corporation, Osaka-fu, both of Japan

[21] Appl. No.: 09/310,858

[22] Filed: May 13, 1999

[30] Foreign Application Priority Data

| May 18, 1998 | [JP] | Japan | 10-135491 |
| May 18, 1998 | [JP] | Japan | 10-135492 |

[51] Int. Cl.$^7$ ................................................. C07C 245/14
[52] U.S. Cl. ................................................. 534/561
[58] Field of Search ................................................. 534/561

[56] References Cited

U.S. PATENT DOCUMENTS

| 3,332,936 | 7/1967 | Diekmann | 534/556 |
| 5,216,135 | 6/1993 | Urano et al. | 534/556 |
| 5,338,641 | 8/1994 | Pawlowski et al. | 430/165 |
| 5,350,660 | 9/1994 | Urano et al. | 430/176 |
| 5,424,166 | 6/1995 | Pawlowski et al. | 430/157 |

FOREIGN PATENT DOCUMENTS

| 2-84648 | 3/1990 | Japan . |
| 2-118655 | 5/1990 | Japan . |
| 2-187764 | 7/1990 | Japan . |
| 1231789 | 5/1971 | United Kingdom . |

*Primary Examiner*—Fiona T. Powers
*Attorney, Agent, or Firm*—Wenderoth, Lind & Ponack, L.L.P.

[57] ABSTRACT

Disclosed is a poly(disulfonyl diazomethane) compound as a class of novel compounds represented by the general formula $$R-SO_2-C(N_2)-SO_2-[Z-SO_2-C(N_2)-SO_2]_n-R,$$

in which the subscript n is 1 to 5, each R is a monovalent hydrocarbon group and Z is a divalent hydrocarbon group. The invention also discloses a chemical-amplification positive-working photoresist composition which comprises the above mentioned poly(disulfonyl diazomethane) compound as the radiation-sensitive acid-generating agent in combination with a film-forming resin capable of being imparted with increased solubility in an aqueous alkaline solution by the interaction with an acid, such as a polyhydroxystyrene resin of which a part of the hydroxyl groups are substituted by acid-dissociable solubility-reducing groups, e.g., tert-butoxycarbonyl groups.

6 Claims, 10 Drawing Sheets

(DISULFONYL DIAZOMETHANE COMPOUNDS)

BACKGROUND OF THE INVENTION

The present invention relates to a novel poly(disulfonyl diazomethane) compound suitable as a radiation-sensitive acid-generating agent in a positive-working chemical-amplification photoresist composition and a photoresist composition containing the same. More particularly, the invention relates to a poly(disulfonyl diazomethane) compound capable of gene-rating bulky sulfonic acid molecules by the irradiation with actinic rays and a positive-working chemical-amplification photoresist composition containing the same capable of giving a patterned resist layer of high pattern resolution having an excellently orthogonal cross sectional profile with high photosensitivity.

It is a trend in recent years that, in the photolithographic patterning technology for the manufacture of semiconductor devices, liquid crystal display panels and the like, so-called chemical-amplification photoresist compositions are more and more widely employed as the photoresist. A chemical-amplification photoresist composition utilizes the catalytic activity of an acid generated from a radiation-sensitive acid-generating agent as an essential ingredient of the photoresist composition in the areas pattern-wise exposed to actinic rays. Accordingly, chemical-amplification photoresist compositions are advantageous in respect of the high photosensitivity and excellent pattern resolution even with a relatively low content of the radiation-sensitive acid-generating agent in the photoresist composition.

Chemical-amplification photoresist compositions, which are classified into the positive-working type and negative-working type, each comprise, in general, a radiation-sensitive acid-generating agent and a film-forming resinous ingredient capable of changing the solubility behavior in an aqueous alkaline solution by interacting with the acid generated from the acid-generating agent in the areas irradiated pattern-wise with actinic rays.

The film-forming resinous ingredient most widely employed in the above mentioned positive-working photoresist composition of the chemical-amplification type is a polyhydroxystyrene resin of which a part of the hydroxyl groups are substituted by acid-dissociable solubility-reducing groups such as tert-butoxycarbonyl group, tetrahydropyranyl group and the like. In the negative-working chemical-amplification photoresist compositions, on the other hand, the film-forming resinous ingredient is usually a combination of a resinous ingredient such as the above mentioned polyhydroxystyrene substituted for a part of the hydroxyl groups by the solubility-reducing groups, polyhydroxystyrene or novolak resin with an acid-crosslinkable compound such as melamine resins, urea resins and the like.

Along with the trend in recent years for an increasing fineness in the photolithographic patterning in the manufacture of semiconductor devices, intensive investigations are now under way for the development of the photolithographic technology capable of accomplishing a fineness of about 0.25 μm in pattern resolution by employing a chemical-amplification positive-working photoresist composition. As to the light source for pattern-wise exposure of the photoresist layer, investigations are also undertaken for the use of KrF excimer laser beams of 248 nm wavelength by which a still finer pattern resolution of smaller than 0.25 μm could be accomplished to comply with the requirement in the semiconductor devices of next generation.

While various types of radiation-sensitive acid-generating compounds have been proposed in the formulation of chemical-amplification positive-working photoresist compositions, diazomethane compounds having a single $-SO_2-C(N_2)-SO_2-$ linkage in the molecule disclosed in U.S. Pat. No. 3,332,936 and British Patent 1,231,789 form a class of promising acid-generating agents in a chemical-amplification photoresist composition as is disclosed in Japanese Patent Kokai 2-118655, 2-84648, 2-187764, 3-103854, 4-210960 and 4-217249.

The above mentioned diazomethane compounds, however, are not quite satisfactory for use in the modern photolithographic patterning works requiring extreme fineness of 0.25 μm or finer in the pattern resolution because such fine resolution of pattern cannot be accomplished by using the diazomethane compound if not to mention the problem of a poor cross sectional profile of the patterned resist layer.

SUMMARY OF THE INVENTION

The present invention accordingly has a primary object to provide a novel diazomethane compound which can overcome the above mentioned disadvantages of conventional diazomethane compounds as an acid-generating agent in a chemical-amplification photoresist composition and is useful as a radiation-sensitive acid-generating agent in a high-performance positive-working photoresist composition of the chemical-amplification type. Another object of the present invention is to provide a novel chemical-amplification positive-working photoresist composition containing the above mentioned novel diazomethane compound as an acid-generating agent.

Thus, the novel diazomethane compound provided by the present invention is a poly(disulfonyl diazomethane) compound represented by the general formula

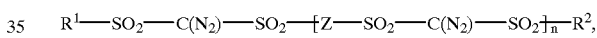

(I)

in which the subscript n is a positive integer not exceeding 5, $R^1$ and $R^2$ are each, independently from the other, a monovalent cyclic hydrocarbon group having 6 to 15 carbon atoms and Z is a divalent hydrocarbon group.

The chemical-amplification positive-working photoresist composition is a uniform blend in the form of a solution which comprises:

(A) 100 parts by weight of a film-forming resinous compound capable of being imparted with an increased solubility in an aqueous alkaline solution by interacting with an acid; and (B) from 0.5 to 20 parts by weight of a poly(disulfonyl diazomethane) compound represented by the general formula

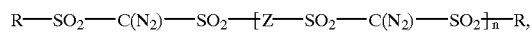

(IA)

in which the subscript n is a positive integer not exceeding 5, each R is, independently from the other, a monovalent hydrocarbon group selected from the group consisting of alkyl groups having 1 to 10 carbon atoms, cycloalkyl groups having 5 to 10 carbon atoms and aromatic hydrocarbon groups having 6 to 15 carbon atoms, and Z is a divalent hydrocarbon group.

DETAILED DESCRIPTION OF THE PREFERRED EMBODIMENTS

Figure 1:
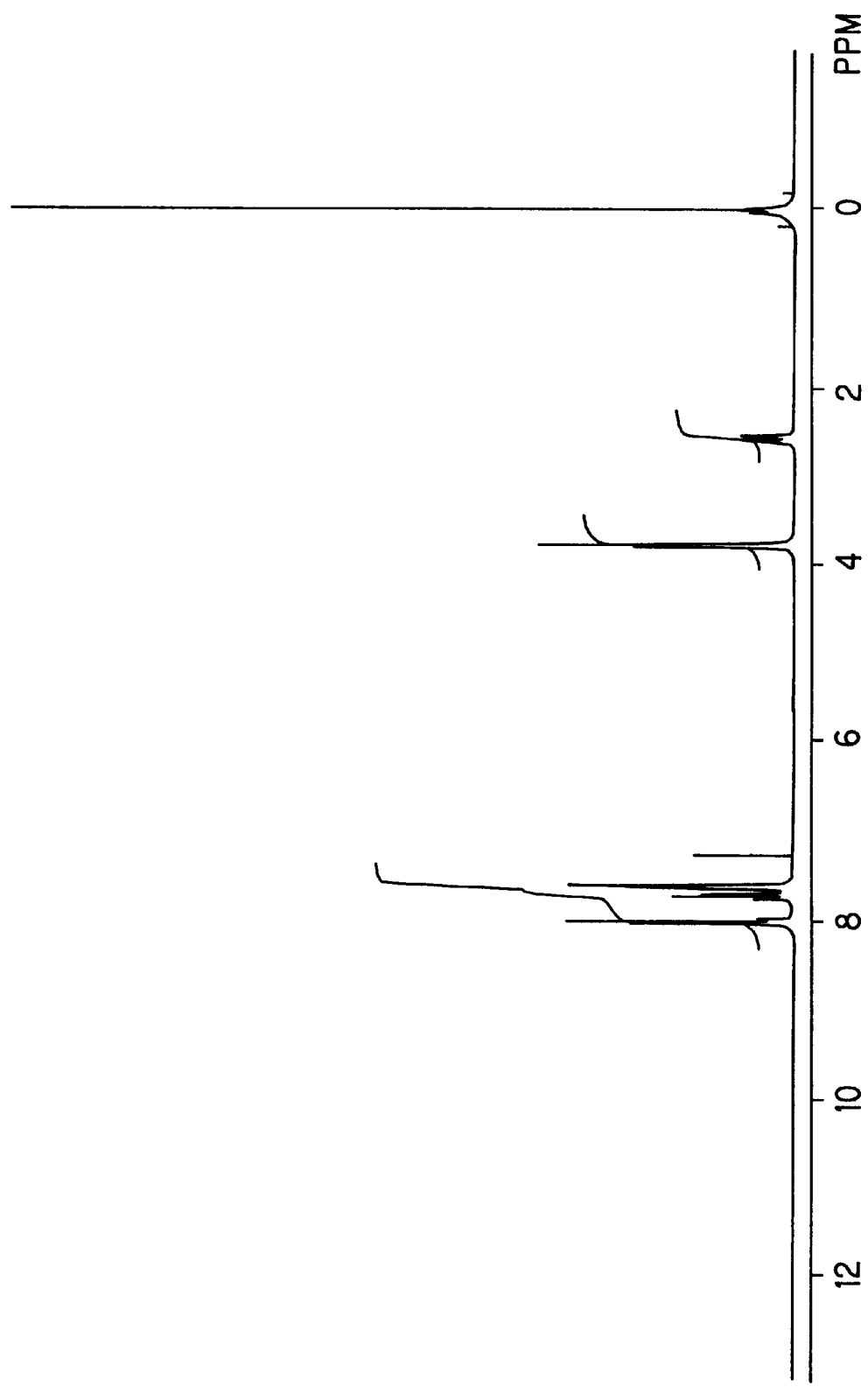
FIG. 1 is a proton NMR spectrum of 1,3-bis (phenylsulfonyl diazomethylsulfonyl) propane prepared in Example 1.

The poly(disulfonyl diazomethane) compound of the present invention represented by the general formula (I), in which each symbol has the meaning defined above, is a novel compound not known in the prior art and not described in any literatures. The monovalent cyclic hydrocarbon group of 6 to 15 carbon atoms denoted by $R^1$ or $R^2$ includes cycloalkyl groups, aryl groups and aralkyl groups. The cycloalkyl group is exemplified by cyclohexyl, cycloheptyl and cyclooctyl groups. The aryl group is exemplified by phenyl and naphthyl groups. The aralkyl group is exemplified by benzyl, phenethyl and naphthylmethyl groups. These cyclic hydrocarbon groups can be substituted for one or more of the hydrogen atoms by a variety of substituent atoms and groups including atoms of halogen such as fluorine, chlorine, bromine and iodine, alkyl groups such as methyl, ethyl, n-propyl, isopropyl, n-butyl, isobutyl and tert-butyl groups and alkoxy groups such as methoxy, ethoxy and propoxy groups as well as halogen-substituted alkyl and alkoxy groups.

The divalent hydrocarbon group denoted by Z in the general formula (I) includes alkylene groups having 1 to 10 carbon atoms exemplified by methylene, ethylene, trimethylene, tetramethylene, pentamethylene, hexamethylene, octamethylene and decamethylene groups as the examples of straightly linear alkylene groups although Z can be a branched alkylene group.

The subscript n in the general formula (I) is a positive integer not exceeding 5 but n is preferably 1 because of the high efficiency in the synthetic preparation process of the compound.

Particular examples of the poly(disulfonyl diazomethane) compound represented by the general formula (I) include the 8 compounds A to H shown below accompanied by the respective structural formulas, in which Ph is a phenyl group and Ch is a cyclohexyl group, and indication of the melting point and/or the decomposition temperature in some of them.

Compound A: 1,3-bis(phenylsulfonyl diazomethylsulfonyl) propane of the formula

having a decomposition temperature of 135° C.

Compound B: 1,4-bis(phenylsulfonyl diazomethylsulfonyl) butane of the formula

having a decomposition temperature of 147° C.

Compound C: 1,6-bis(phenylsulfonyl diazomethylsulfonyl) hexane of the formula

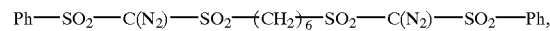

having a melting point of 132° C. and decomposition temperature of 145° C.

Compound D: 1,10-bis(phenylsulfonyl diazomethylsulfonyl) decane of the formula

having a decomposition temperature of 147° C.

Compound E: 1,2-bis(cyclohexylsulfonyl diazomethylsulfonyl) ethane of the formula

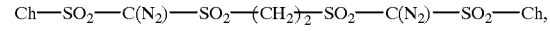

having a decomposition temperature of 149° C.

Compound F: 1,3-bis(cyclohexylsulfonyl diazomethylsulfonyl) propane of the formula

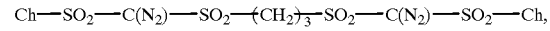

having a decomposition temperature of 153° C.

Compound G: 1,6-bis(cyclohexylsulfonyl diazomethylsulfonyl) hexane of the formula

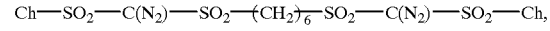

having a melting point of 109° C. and decomposition temperature of 122° C.

Compound H: 1,10-bis(cyclohexylsulfonyl diazomethylsulfonyl) decane of the formula

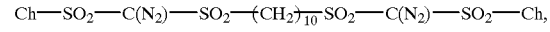

having a decomposition temperature of 116° C.

The poly(disulfonyl diazomethane) compound represented by the general formula (I) can be prepared by the synthetic method described below by taking a particular compound in which the groups denoted by $R^1$ and $R^2$ are each a phenyl group Ph and the subscript n is 1 as an example. The synthetic procedure is expressed by the following reaction equations, in which X is a halogen atom and the subscript m is a positive integer not exceeding 10.

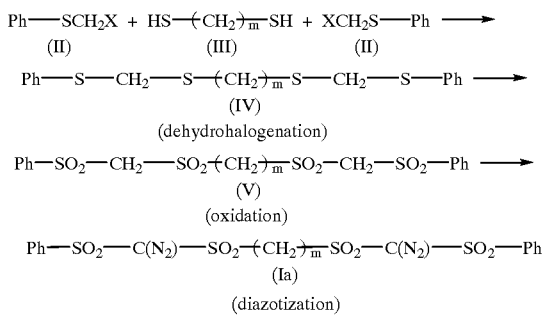

$$\text{Ph-SCH}_2\text{X} + \text{HS-(CH}_2\text{)}_m\text{-SH} + \text{XCH}_2\text{S-Ph} \longrightarrow$$
$$(\text{II}) \quad (\text{III}) \quad (\text{II})$$

$$\text{Ph-S-CH}_2\text{-S-(CH}_2\text{)}_m\text{-S-CH}_2\text{-S-Ph} \longrightarrow$$
$$(\text{IV})$$
(dehydrohalogenation)

$$\text{Ph-SO}_2\text{-CH}_2\text{-SO}_2\text{-(CH}_2\text{)}_m\text{-SO}_2\text{-CH}_2\text{-SO}_2\text{-Ph} \longrightarrow$$
$$(\text{V})$$
(oxidation)

$$\text{Ph-SO}_2\text{-C(N}_2\text{)-SO}_2\text{-(CH}_2\text{)}_m\text{-SO}_2\text{-C(N}_2\text{)-SO}_2\text{-Ph}$$
$$(\text{Ia})$$
(diazotization)

In the first place, namely, 2 moles of an α-halogenothioanisole (II) are reacted with 1 mole of an α,ω-alkane-dithiol (III) in an inert solvent such as an aromatic hydrocarbon solvent, e.g., toluene, in the presence of a hydrogen halide acceptor to give the compound of the general formula (IV), which is then, in a suitable organic solvent, oxidized with an oxidizing agent such as hydrogen peroxide to give the α,ω-bis(phenylsulfonylmethyl sulfonyl) alkane of the general formula (V). This compound (V) is diazotized in a suitable organic solvent with a diazotizing agent such as tosyl azide to give the α,ω-bis (phenylsulfonyl diazomethyl sulfonyl) alkane compound (Ia) which is isolated from the reaction mixture and purified by a known method.

The hydrogen halide acceptor used in the dehydrohalogenation reaction is preferably an alkali hydroxide. The oxidation reaction of the compound (IV) by an oxidizing agent such as hydrogen peroxide to give the α,ω-bis (phenylsulfonylmethyl sulfonyl) alkane of the general formula (V) can be promoted by the use of a catalyst such as an alkali tungstate. The diazotization reaction of this compound (V) by tosyl azide to give the α,ω-bis (phenylsulfonyldiazomethyl sulfonyl) alkane compound (Ia) is performed usually in the presence of an alkaline compound such as an alkali hydroxide.

When the groups $R^1$ and $R^2$ are each a cyclohexyl group and the subscript n is 1, α-halogenothioanisole is replaced with cyclohexane thiol which is reacted with bromochloromethane to give cyclohexyl methoxy methyl sulfide. This sulfide compound is reacted with an α,ω-alkane dithiol in the presence of sulfuric acid to give a compound corresponding to the compound (IV) by replacement of the phenyl group with a cyclohexyl group. This compound can be oxidized and diazotized in the same manner as above to give an α,ω-bis(cyclohexylsulfonyl diazomethyl sulfonyl) alkane compound.

It is known that conventional bis(cyclohexylsulfonyl) diazomethane compounds are dediazotized when irradiated with actinic rays in the presence of water to form a sulfonic acid by the rearrangement reaction according to the following reaction equation, in which Ch is a cyclohexyl group.

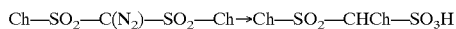

$$\text{Ch-SO}_2\text{-C(N}_2\text{)-SO}_2\text{-Ch} \rightarrow \text{Ch-SO}_2\text{-CHCh-SO}_3\text{H}$$

In contrast thereto, it is presumable that the poly (disulfonyl diazomethane) compound of the general formula (I), in which the subscript n is 1, causes a rearrangement reaction according to the following reaction scheme when irradiated with actinic rays in the presence of water.

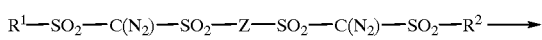

$$R^1\text{-SO}_2\text{-C(N}_2\text{)-SO}_2\text{-Z-SO}_2\text{-C(N}_2\text{)-SO}_2\text{-R}^2 \longrightarrow$$

-continued

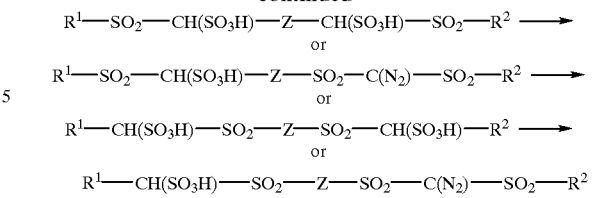

$$R^1\text{-SO}_2\text{-CH(SO}_3\text{H)-Z-CH(SO}_3\text{H)-SO}_2\text{-R}^2 \longrightarrow$$
or
$$R^1\text{-SO}_2\text{-CH(SO}_3\text{H)-Z-SO}_2\text{-C(N}_2\text{)-SO}_2\text{-R}^2 \longrightarrow$$
or
$$R^1\text{-CH(SO}_3\text{H)-SO}_2\text{-Z-SO}_2\text{-CH(SO}_3\text{H)-R}^2 \longrightarrow$$
or
$$R^1\text{-CH(SO}_3\text{H)-SO}_2\text{-Z-SO}_2\text{-C(N}_2\text{)-SO}_2\text{-R}^2$$

It would be a due presumption that, when the poly (disulfonyl diazomethane) compound of the general formula (I) where n is 2 to 5 is irradiated with actinic rays in the presence of water, the group $-SO_2-C(N_2)-SO_2-$ is converted fully or only partly into sulfonic acid groups.

In contrast to conventional diazomethane compounds having only one $-SO_2-C(N_2)-SO_2-$ group in the molecule, as is described above, the molecule of the sulfonic acid produced from the poly(disulfonyl diazomethane) compound of the present invention has increased bulkiness so that it would be a due assumption that, when the photolithographic patterning is performed by using a chemical-amplification positive-working photoresist composition containing the same, the patterned resist layer could have excellent pattern resolution and good orthogonality of the cross sectional profile as a consequence of a decrease in the mobility of the sulfonic acid molecules generated by the light exposure in the post-exposure baking treatment.

The chemical-amplification positive-working photoresist composition, which has been developed on the base of the above mentioned prospect, is a uniform blend in the form of a solution which comprises:

(A) 100 parts by weight of a film-forming resinous compound capable of being imparted with an increased solubility in an aqueous alkaline solution by interacting with an acid; and (B) from 0.5 to 20 parts by weight of a poly(disulfonyl diazomethane) compound represented by the general formula

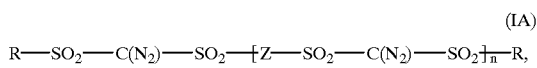

$$R-SO_2-C(N_2)-SO_2-[Z-SO_2-C(N_2)-SO_2]_n-R, \quad (\text{IA})$$

in which the subscript n is a positive integer not exceeding 5, each R is, independently from the other, a monovalent hydrocarbon group selected from the group consisting of alkyl groups having 1 to 10 carbon atoms, cycloalkyl groups having 5 to 10 carbon atoms and aromatic hydrocarbon groups having 6 to 15 carbon atoms, and Z is a divalent hydrocarbon group.

The film-forming resinous compound as the component (A) is typically exemplified by polymeric resins having phenolic hydroxyl groups or carboxyl groups protected or substituted by acid-dissociable solubility-reducing groups.

Various kinds of acid-dissociable solubility-reducing groups are known in the art and any of them can be used in the present invention without particular limitations. Particular examples of the acid-dissociable solubility-reducing group include tertiary alkoxycarbonyl groups such as tert-butoxycarbonyl and tert-amyloxycarbonyl groups, tertiary alkyl groups such as tert-butyl and tert-amyl groups, tertiary alkoxycarbonylalkyl groups such as tert-butoxycarbonylmethyl and tert-amyloxycarbonylmethyl groups, acetal groups such as tetrahydropyranyl and tetrahydrofuranyl groups, 1-alkoxyalkyl groups such as 1-ethoxyethyl and 1-methoxy-n-propyl groups, silyl ether groups such as trimethylsilyl group, and so on, of which tertiary alkoxycarbonyl groups, tertiary alkyl groups, acetal groups and 1-alkoxyalkyl groups are preferable and tert-butoxycarbonyl, tert-butyl, tetrahydrofuranyl, tetrahydropyranyl and 1-ethoxyethyl groups are particularly preferable.

Several classes of resinous compounds are suitable as the component (A) including:

(A1) polyhydroxystyrene resins, of which from 10 to 50% or, preferably, from 15 to 35% of the hydroxyl hydrogen atoms are substituted by tert-butoxycarbonyl groups;

(A2) polyhydroxystyrene resins, of which from 10 to 50% or, preferably, from 15 to 35% of the hydroxyl hydrogen atoms are substituted by tert-butoxycarbonylmethyl groups;

(A3) polyhydroxystyrene resins, of which from 10 to 50% or, preferably, from 15 to 35% of the hydroxyl hydrogen atoms are substituted by tetrahydropyranyl groups;

(A4) polyhydroxystyrene resins, of which from 10 to 50% or, preferably, from 15 to 35% of the hydroxyl hydrogen atoms are substituted by alkoxyalkyl groups such as 1-ethoxyethyl and 1-methoxy-n-propyl groups; and (A5) copolymeric resins obtained from hydroxystyrene, styrene and tert-butyl methacrylate.

Although the above described classes of the film-forming resinous compounds can be used as the component (A) either singly or as a mixture of two kinds or more, it is preferable that the component (A) is a combination of a resin of the class (A1) and a resin of the class (A4) or a combination of a resin of the class (A3) and a resin of the class (A4) in a weight proportion of the class (A1) resin or class (A3) resin to the class (A4) resin in the range from 5:95 to 50:50 or, preferably, from 10:90 to 30:70.

The component (B) in the chemical-amplification positive-working photoresist composition of the present invention is a radiation-sensitive acid-generating agent which is preferably a poly(disulfonyl diazomethane) compound represented by the above given general formula (IA), in which each of the groups denoted by R is a monovalent group selected from the group consisting of straightly linear or branched alkyl groups having 1 to 10 carbon atoms, cycloalkyl groups having 5 to 10 carbon atoms and aromatic hydrocarbon groups having 6 to 15 carbon atoms. Cycloalkyl, aryl and aralkyl groups, which can be unsubstituted or substituted, are preferred as the group denoted by R.

When the above mentioned preferable groups are substituted hydrocarbon groups, the substituent group is exemplified by atoms of halogen including fluorine, chlorine, bromine and iodine, alkyl groups including methyl, ethyl, n-propyl, isopropyl, n-butyl, isobutyl and tert-butyl groups and alkoxy groups including methoxy, ethoxy and propoxy groups as well as halogenated alkyl and alkoxy groups.

Since the photoresist composition generally should have transparency to the excimer laser beams of 248 nm wavelength as high as possible in order to accomplish high pattern resolution, the group R is, preferably, an alkyl or cycloalkyl group or, more preferably, a cyclohexyl group. When the substrate surface is provided with a coating film of a metal such as aluminum having high reflectivity, however, the transparency of the photoresist layer should have relatively low transparency in order to reduce the phenomenon of halation so that aryl groups having 6 to 15 carbon atoms can be used as the group R. Phenyl group is also preferable as the group R in respect of a relatively large focusing depth latitude.

The divalent hydrocarbon group denoted by Z in the general formula (IA) is preferably a straightly linear or branched alkylene group or, preferably, a polymethylene group having 1 to 10 carbon atoms. The subscript n is preferably 1 in respect of the good efficiency in the synthetic procedure and the high effectiveness of the compound as a radiation-sensitive acid-generating agent.

Particularly preferable poly(disulfonyl diazomethane) compound as the component (B) are those represented by the general formula (IA) in which each R is a cyclohexyl group or a phenyl group, the subscript n is 1 and Z is a polymethylene group. Examples of these compounds in which R is a cyclohexyl group include 1,2-bis (cyclohexylsulfonyl diazomethylsulfonyl) ethane, 1,3-bis (cyclohexylsulfonyl diazomethylsulfonyl) propane, 1,6-bis (cyclohexylsulfonyl diazomethylsulfonyl) hexane and 1,10-bis(cyclohexylsulfonyl diazomethylsulfonyl) decane. Examples of the compounds in which R is a phenyl group include 1,3-bis(phenylsulfonyl diazomethylsulfonyl) propane, 1,4-bis(phenylsulfonyl diazomethylsulfonyl) butane, 1,6-bis(phenylsulfonyl diazomethylsulfonyl) hexane and 1,10-bis(phenylsulfonyl diazomethylsulfonyl) decane. These poly(disulfonyl diazomethane) compounds can be used as the component (B) either singly or as a combination of two kinds or more according to need. It is also optional that the component (B) is combined with a conventional acid-generating agent, if compatible.

The amount of the radiation-sensitive acid-generating agent as the component (B) in the inventive photoresist composition is, usually, in the range from 0.5 to 20 parts by weight or, preferably, from 1 to 10 parts by weight per 100 parts by weight of the component (A). When the amount thereof is too small, complete patterning can hardly be accomplished. When the amount thereof is too large, on the other hand, difficulties are encountered in the preparation of a homogeneous solution of the photoresist composition due to the limited solubility of the compound in the organic solvent or, even if a homogeneous solution could be formed, a decrease is caused in the storage stability of the photoresist solution.

Besides the above described components (A) and (B) as the essential ingredients, the inventive photoresist composition can be compounded, according to need, with other additive compounds including an amine compound which serves to prevent diffusion of the acid generated from the acid-generating agent in the areas irradiated with actinic rays and to improve the stability of the latent images formed in the photoresist layer exposed to actinic rays before being subjected to a post-exposure baking treatment and further additionally a carboxylic acid which serves to improve the photosensitivity of the photoresist composition and to decrease the dependency of the cross sectional profile of the patterned resist layer on the nature of the substrate surface layer which may be a coating film of silicon nitride (SiN), boron-phosphorus-silicate glass (BPSG) or titanium nitride (TiN). It is sometimes the case that the substrate surface is provided with a reflection preventing layer of an organic or inorganic material.

It is usual that the inventive photoresist composition is prepared in the form of a homogeneous solution by dissolving the essential and optional ingredients in an organic solvent which can be applied to the substrate surface. Examples of suitable organic solvents include ketone solvents such as acetone, methyl ethyl ketone, cyclohexanone, methyl isoamyl ketone and 2-heptanone, polyhydric alcohols and derivatives thereof such as ethyleneglycol, ethyleneglycol monoacetate, diethyleneglycol, diethyleneglycol monoacetate, propyleneglycol, propyleneglycol monoacetate, dipropyleneglycol and dipropyleneglycol monoacetate as well as monomethyl, monoethyl, monopropyl, monobutyl and monophenyl ethers thereof, cyclic ether solvents such as dioxane and ester solvents such as methyl lactate, ethyl lactate, methyl acetate, ethyl acetate, butyl acetate, methyl pyruvate, ethyl pyruvate, methyl methoxypropionate and ethyl ethoxypropionate, which can be used either singly or as a mixture of two kinds or more.

Various known additives having compatibility can optionally be added to the photoresist composition of the invention each in a limited amount including auxiliary resins to improve the properties of the resist layer, plasticizers, stabilizers, coloring agents, surface active agents and so on.

The photolithographic patterning procedure by using the inventive photoresist composition is not particularly different from the procedure by using a conventional photoresist composition. For example, namely, the surface of a substrate such as a semiconductor silicon wafer is coated with the inventive photoresist composition on a suitable coating machine such as a spinner followed by a drying treatment to form a dried photoresist layer, which is then pattern-wise exposed to actinic rays such as KrF excimer laser beams on a minifying projection exposure machine through a pattern-bearing photomask followed by a post-exposure baking treatment to form a latent image in the photoresist layer. The latent images are developed by a development treatment using an aqueous alkaline developer solution such as a 1 to 10% by weight aqueous solution of tetramethylammonium hydroxide to selectively dissolve away the photoresist layer in the exposed areas leaving a patterned resist layer having high fidelity to the photomask pattern and an excellently orthogonal cross sectional profile with very fine pattern resolution of 0.15 to 0.22 μm fineness.

In the following, the present invention is described in more detail by way of examples, which, however, never limit the scope of the invention in any way. In the Examples and Comparative Examples given below, the term of "parts" always refers to "parts by weight".

EXAMPLE 1

1,3-Bis(phenylsulfonyl diazomethylsulfonyl) propane was prepared in the manner described below.

Thus, 16.2 g (0.15 mole) of 1,3-propane dithiol were added dropwise to a solution of 19.5 g (0.35 mole) of potassium hydroxide in 200 ml of ethyl alcohol kept at 20 to 30° C. followed by further continued agitation of the solution for 1 hour at the same temperature. In the next place, 47.6 g (0.30 mole) of α-chlorothioanisole were added dropwise to the solution kept at 30 to 50° C. taking 20 minutes followed by further continued agitation of the reaction mixture for 30 minutes at the same temperature. The reaction mixture was then diluted by the addition of 1000 ml of water and extracted with 700 ml of ethyl acetate. After washing successively with diluted hydrochloric acid and water, the organic extract solution was dried over anhydrous magnesium sulfate and freed from the solvent by distillation to give 49.4 g of a light yellow material which could be identified to be 1,3-bis(phenylthiomethylthio) propane. The above mentioned yield of this product corresponded to 94% of the theoretical value.

In the next place, 165.0 g (1.70 moles) of a 35% by weight aqueous solution of hydrogen peroxide were added dropwise to a mixture of 49.4 g (0.14 mole) of the above obtained 1,3-bis(phenylthiomethylthio) propane in 420 ml of acetic acid at 70 to 100° C. taking 30 minutes followed by further continued agitation of the reaction mixture for 1 hour at 90 to 100° C. After cooling to room temperature, the reaction mixture was admixed with 700 ml of water and the crystalline precipitates were collected by filtration, washed with water and dried to give 48.1 g of a white crystalline material which could be identified to be 1,3-bis(phenylsulfonyl methylsulfonyl) propane. The above mentioned yield of this product corresponded to 71% of the theoretical value.

In the next place, 200 g (0.22 mole) of a 6.2% by weight aqueous solution of potassium hydroxide were added dropwise to a mixture of 48.1 g (0.10 mole) of the above obtained 1,3-bis(phenylsulfonyl methylsulfonyl) propane and 1000 ml of acetonitrile kept at −10 to 0° C. taking 5 minutes followed by further continued agitation of the reaction mixture for 15 minutes at the same temperature. Further, the reaction mixture was admixed with 37.5 g (0.19 mole) of tosyl azide at −10° C. followed by further continued agitation of the reaction mixture for 10 minutes at −10 to 0° C. Then, the reaction mixture was poured into 8000 ml of water and the crystalline precipitates were collected by filtration and recrystallized from acetone/water to give 8.7 g of a light yellow crystalline product having a decomposition temperature of 135° C., which could be identified to be 1,3-bis (phenylsulfonyl diazomethylsulfonyl) propane. The above mentioned yield of this product corresponded to 16% of the theoretical value.

Figure 2:
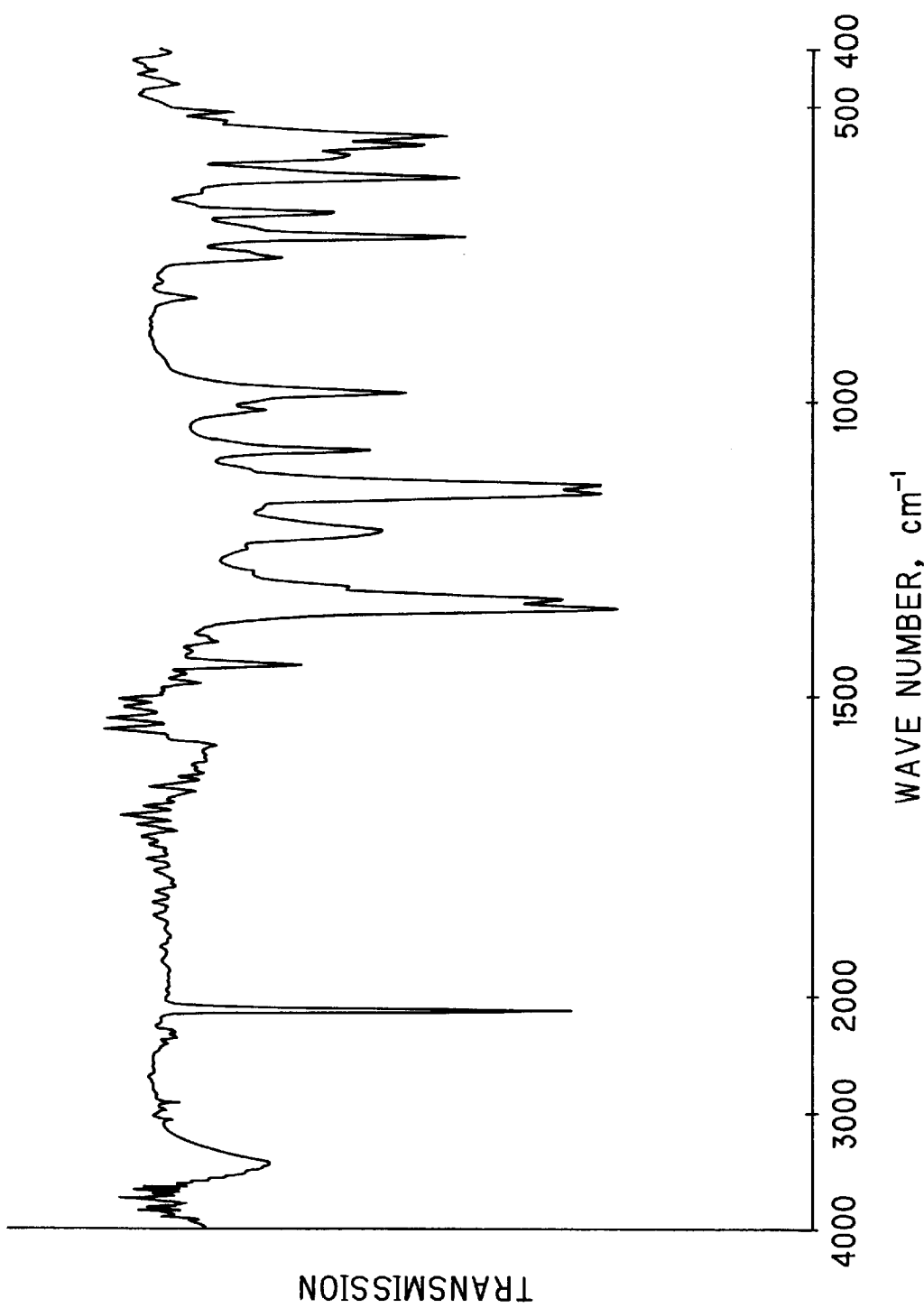
FIG. 2 is an infrared absorption spectrum of 1,3-bis(phenylsulfonyl diazomethylsulfonyl) propane prepared in Example 1.

FIG. 1 and FIG. 2 of the accompanying drawing show a proton NMR spectrum and an infrared absorption spectrum, respectively, of this compound.

EXAMPLE 2

1,4-Bis(phenylsulfonyl diazomethylsulfonyl) butane was prepared in substantially the same manner as in Example 1 excepting for the replacement of 1,3-propane dithiol with the same molar amount of 1,4-butane dithiol. This product as prepared had a decomposition temperature of 147° C.

Figure 3:
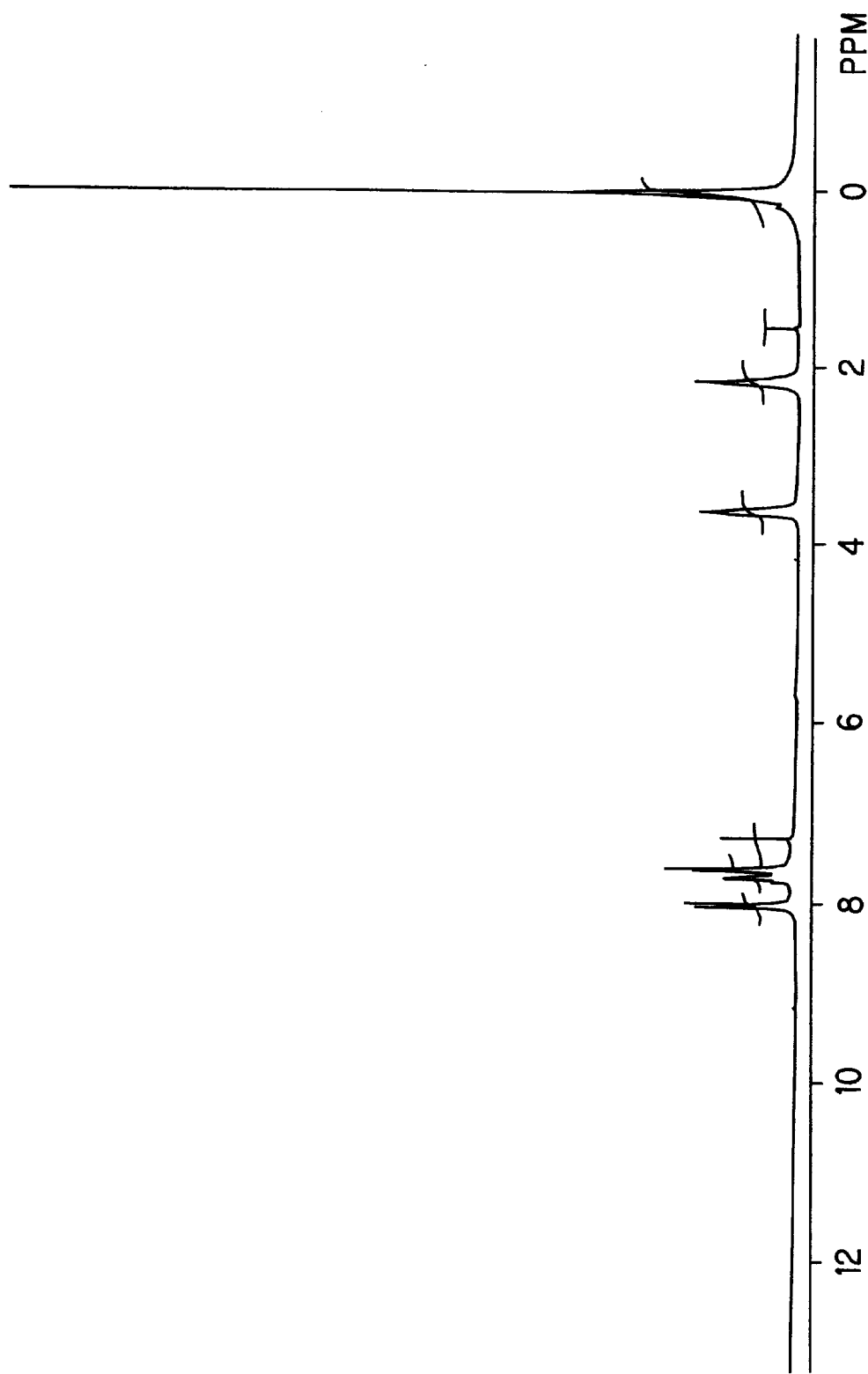
FIG. 3 is a proton NMR spectrum of 1,4-bis(phenylsulfonyl diazomethylsulfonyl) butane prepared in Example 2.
Figure 4:
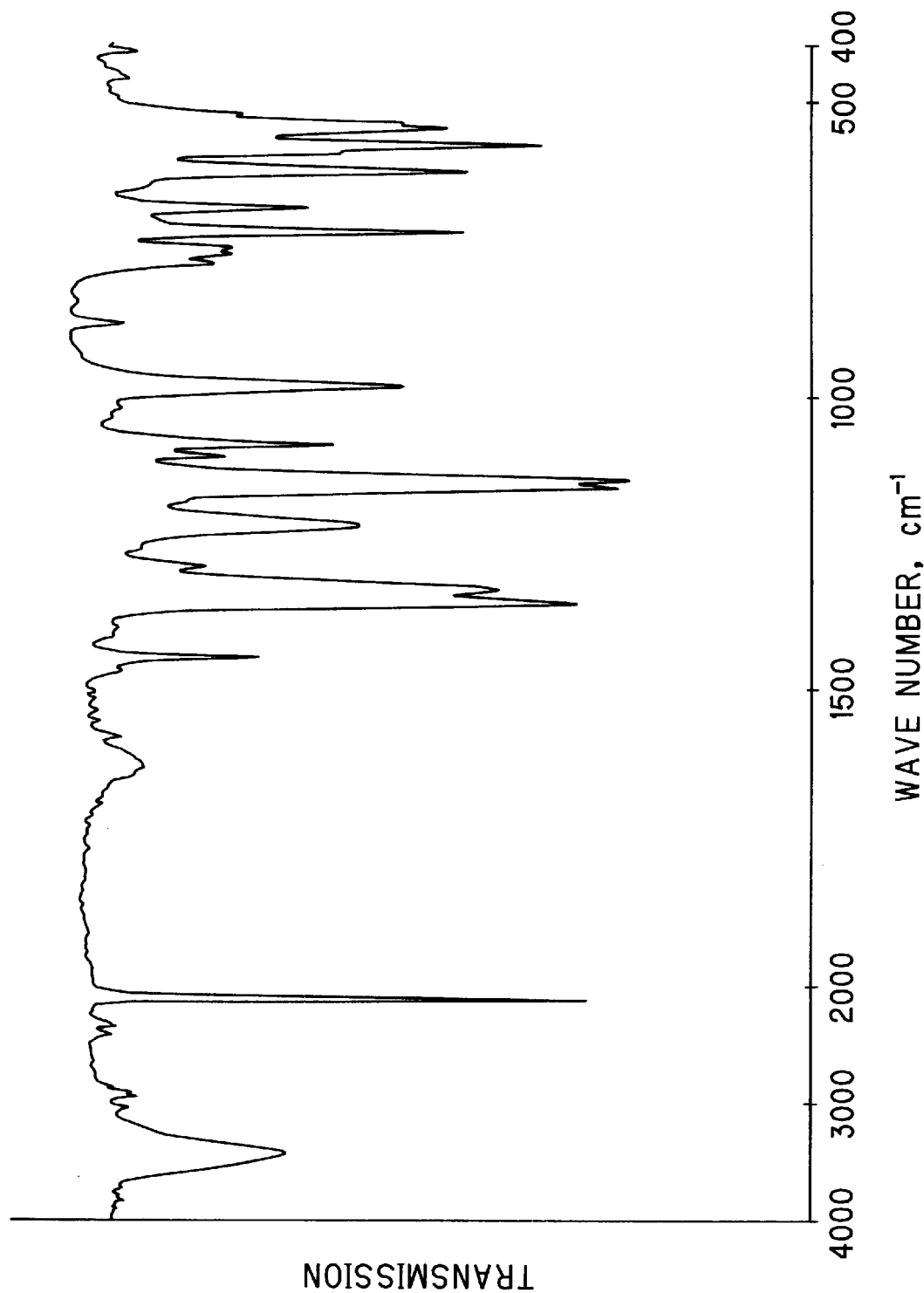
FIG. 4 is an infrared absorption spectrum of 1,4-bis(phenylsulfonyl diazomethylsulfonyl) butane prepared in Example 2.

FIG. 3 and FIG. 4 of the accompanying drawing show a proton NMR spectrum and an infrared absorption spectrum, respectively, of this compound.

EXAMPLE 3

1,6-Bis(phenylsulfonyl diazomethylsulfonyl) hexane was prepared in substantially the same manner as in Example 1 excepting for the replacement of 1,3-propane dithiol with the same molar amount of 1,6-hexane dithiol. This product as prepared had a melting point of 132° C. and decomposition temperature of 146° C.

Figure 5:
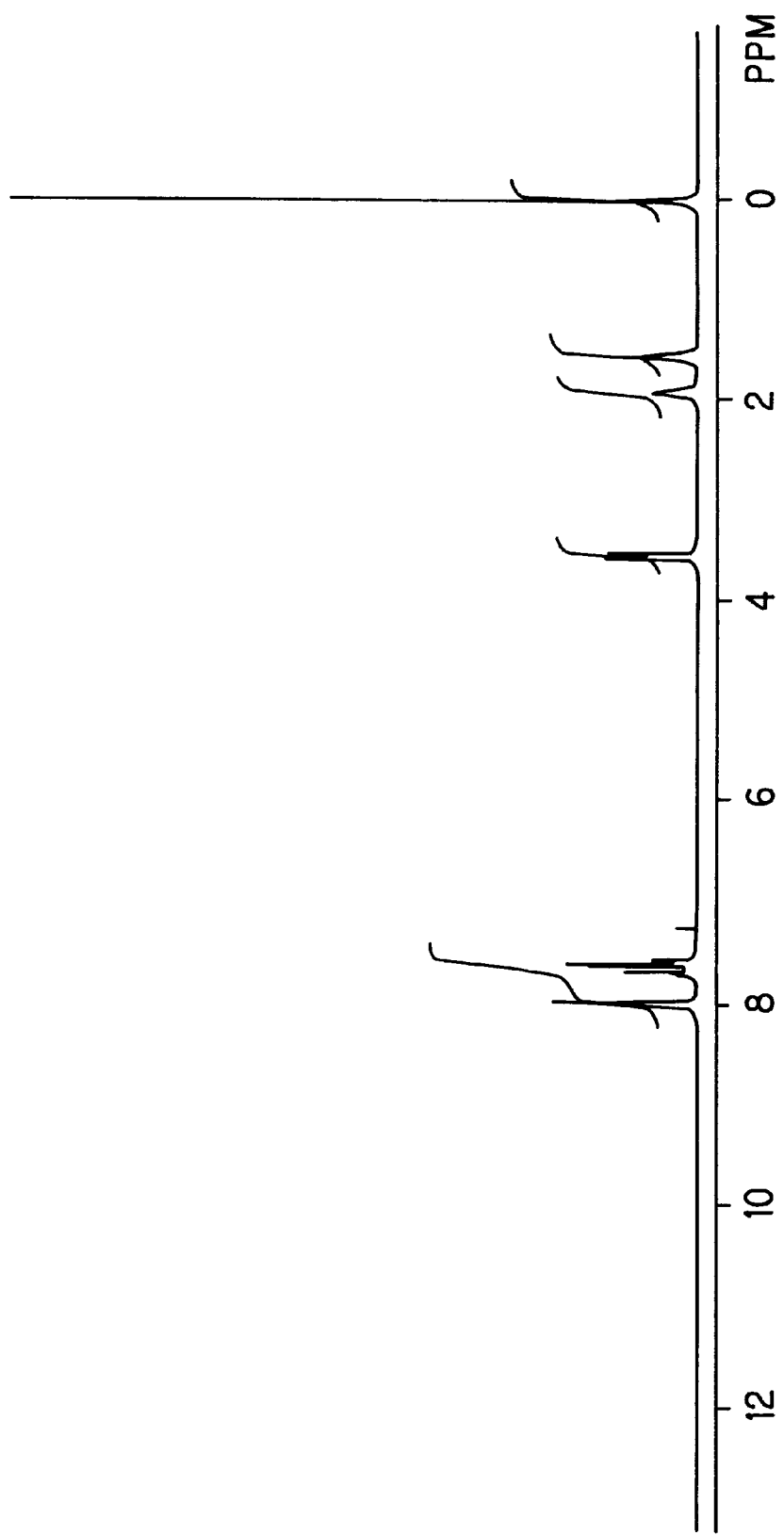
FIG. 5 is a proton NMR spectrum of 1,6-bis(phenylsulfonyl diazomethylsulfonyl) hexane prepared in Example 3.
Figure 6:
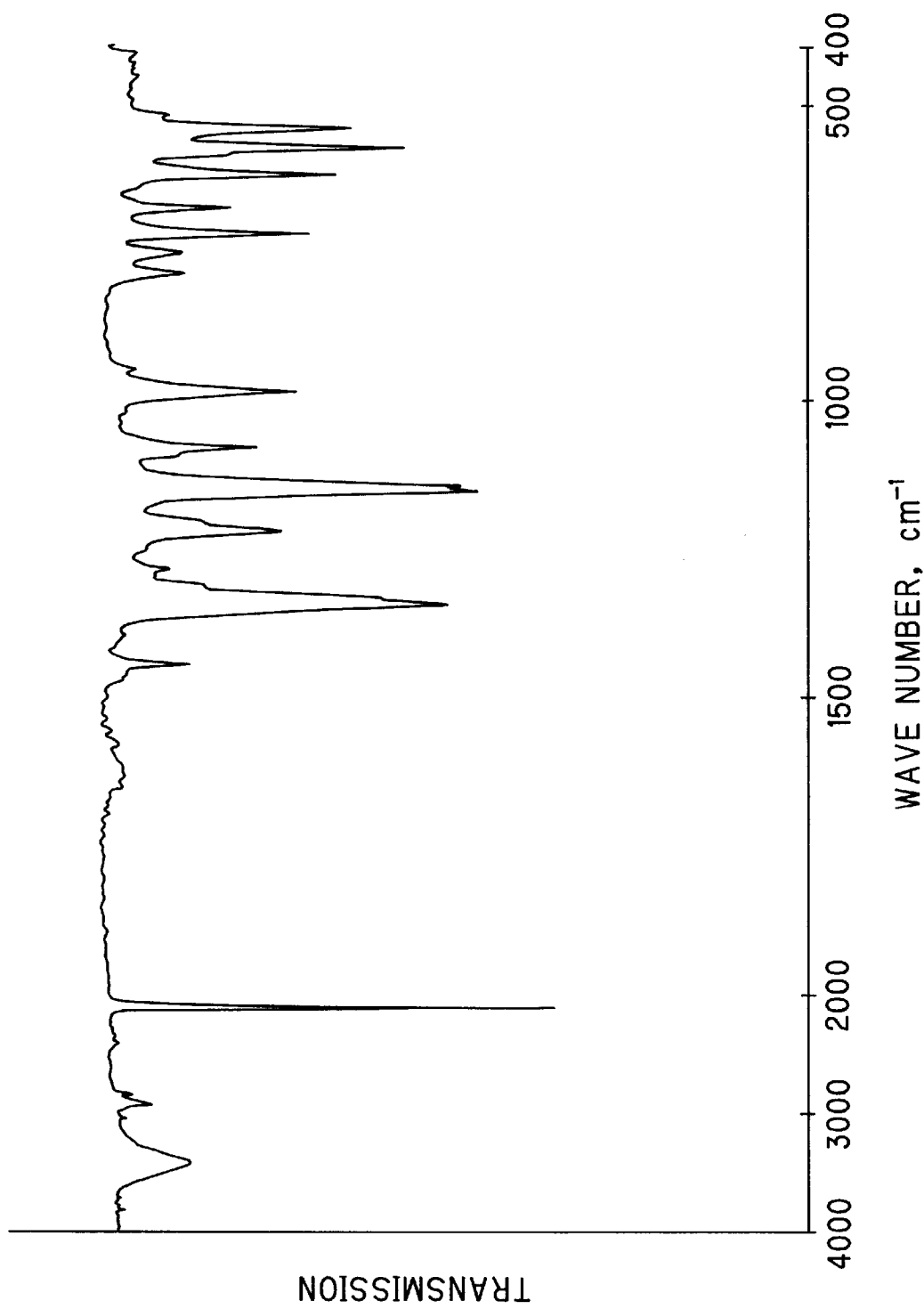
FIG. 6 is an infrared absorption spectrum of 1,6-bis(phenylsulfonyl diazomethylsulfonyl) hexane prepared in Example 3.

FIG. 5 and FIG. 6 of the accompanying drawing show a proton NMR spectrum and an infrared absorption spectrum, respectively, of this compound.

EXAMPLE 4

1,10-Bis(phenylsulfonyl diazomethylsulfonyl) decane was prepared in substantially the same manner as in Example 1 excepting for the replacement of 1,3-propane dithiol with the same molar amount of 1,10-decane dithiol. This product as prepared had a decomposition temperature of 147° C.

Figure 7:
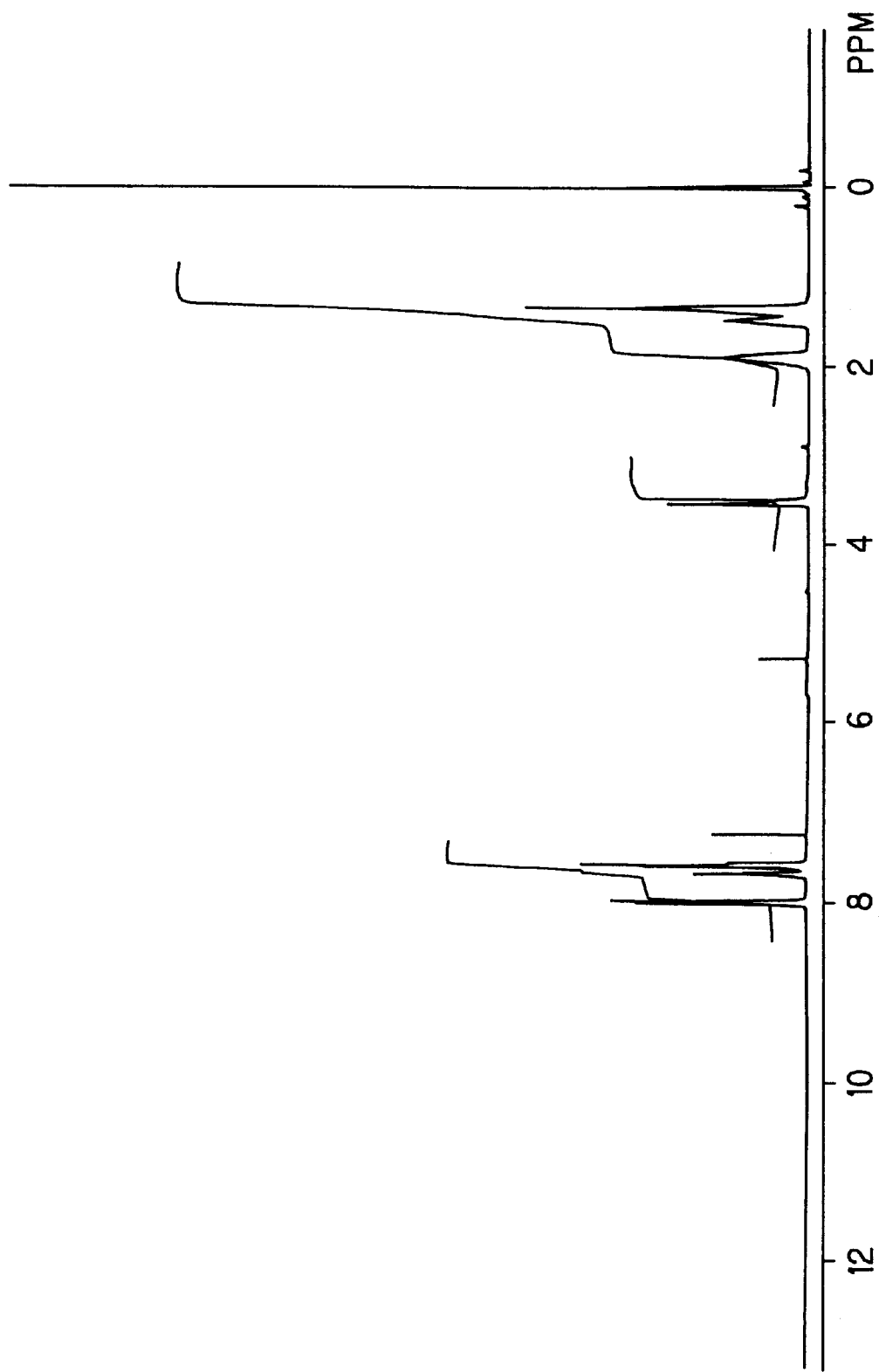
FIG. 7 is a proton NMR spectrum of 1,10-bis(phenylsulfonyl diazomethylsulfonyl) decane prepared in example 4.
Figure 8:
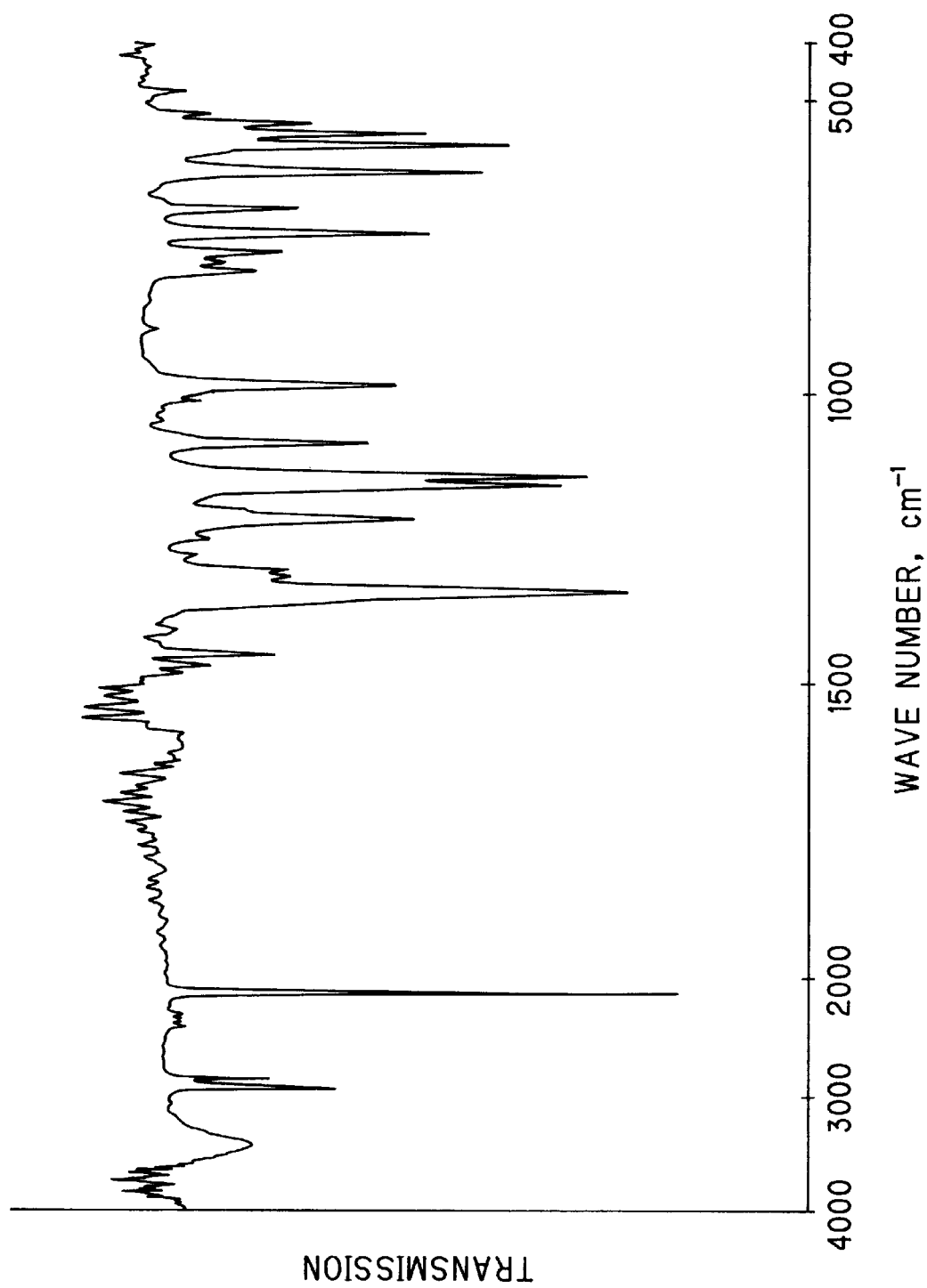
FIG. 8 is an infrared absorption spectrum of 1,10-bis(phenylsulfonyl diazomethylsulfonyl) decane prepared in Example 4.

FIG. 7 and FIG. 8 of the accompanying drawing show a proton NMR spectrum and an infrared absorption spectrum, respectively, of this compound.

EXAMPLE 5

1,6-Bis(cyclohexylsulfonyl diazomethylsulfonyl) hexane was prepared in the manner described below.

Thus, a mixture of 58.1 g (0.50 mole) of cyclohexane thiol, 71.0 g (1.25 moles) of sodium methoxide (95% by weight concentration) and 300 ml of methyl alcohol was added dropwise to a mixture of 600 g of bromochloromethane and 100 ml of methyl alcohol kept at 30 to 35° C. over a period of 3 hours followed by further continued agitation of the mixture for 2 hours at the same temperature. The reaction mixture was admixed with 700 ml of water and, after phase separation into aqueous and organic phases, the organic solution was washed successively with a diluted aqueous sodium hydroxide solution and water followed by drying over anhydrous magnesium sulfate and removal of the solvent by distillation to give 80.1 g of a colorless oily liquid which contained cyclohexyl methoxymethyl sulfide in a purity of 60% corresponding to a gross yield of 100%.

In the next place, 14.9 g (0.15 mole) of 98% sulfuric acid were added dropwise to a mixture of 80.1 g (0.30 mole calculated for 100% purity) of the above obtained cyclohexyl methoxymethyl sulfide, 22.5 g (0.15 mole) of 1,6-hexane dithiol and 220 ml of acetonitrile kept at 15 to 20° C. taking 15 minutes followed by further continued agitation for 1 hour at the same temperature. The reaction mixture was diluted with 500 ml of water and subjected to an extraction treatment with 700 ml of ethyl acetate. After washing successively with a diluted aqueous solution of sodium hydroxide and water, the organic extract solution was dried over anhydrous magnesium sulfate followed by removal of the solvent by distillation to give 86.3 g of a colorless oily liquid which contained 1,6-bis(cyclohexylthio methylthio) hexane in a purity of 37% corresponding to a gross yield of 142% of the theoretical value.

In the next place, 560 g (4.94 moles) of a 30% by weight aqueous solution of hydrogen peroxide were added dropwise to a mixture of 85.4 g (0.08 mole calculated for 100% purity) of the above obtained 1,6-bis(cyclohexylthio methylthio) hexane, 1.0 g of sodium tungstate and 1200 ml of acetic acid kept at 50 to 60° C. over a period of 1.5 hours followed by further continued agitation of the reaction mixture for 6 hours at 60 to 65° C. After cooling to room temperature, the reaction mixture was admixed with 430 ml of water and the crystalline precipitates were collected by filtration, washed with water and dried to give 60 g of a crude crystalline material which was subjected to a suspension purification treatment successively with chloroform and ethyl alcohol to give 29.0 g of a yellow crystalline material which could be identified to be 1,6-bis(cyclohexylsulfonyl methylsulfonyl) hexane having a purity of 92%. The above mentioned yield of this product corresponded to a gross value of 70% based on the theoretical value.

Thereafter, an aqueous solution of 6.2 g (0.11 mole) of potassium hydroxide was added dropwise to a suspension of 26.7 g (0.05 mole) of the above obtained 1,6-bis(cyclohexylsulfonyl methylsulfonyl) hexane and 19.7 g (0.10 mole) of tosyl azide in 200 ml of acetonitrile at 0 to 5° C. over a period of 1 hour followed by further continued agitation of the reaction mixture at 5 to 15° C. for 3 hours. The crystalline precipitates in the reaction mixture were collected by filtration, washed with water and dried to give a crude crystalline product. A 10 g portion of this crude product was subjected to purification by recrystallization from acetonitrile/water to give 8.4 g of a slightly yellowish crystalline material having a melting point of 109° C. and decomposition temperature of 122° C., which could be identified to be 1,6-bis(cyclohexylsulfonyl diazomethylsulfonyl) hexane in a purity of 97%. The above mentioned yield of this product corresponded to 28.7% of the theoretical value.

Figure 9:
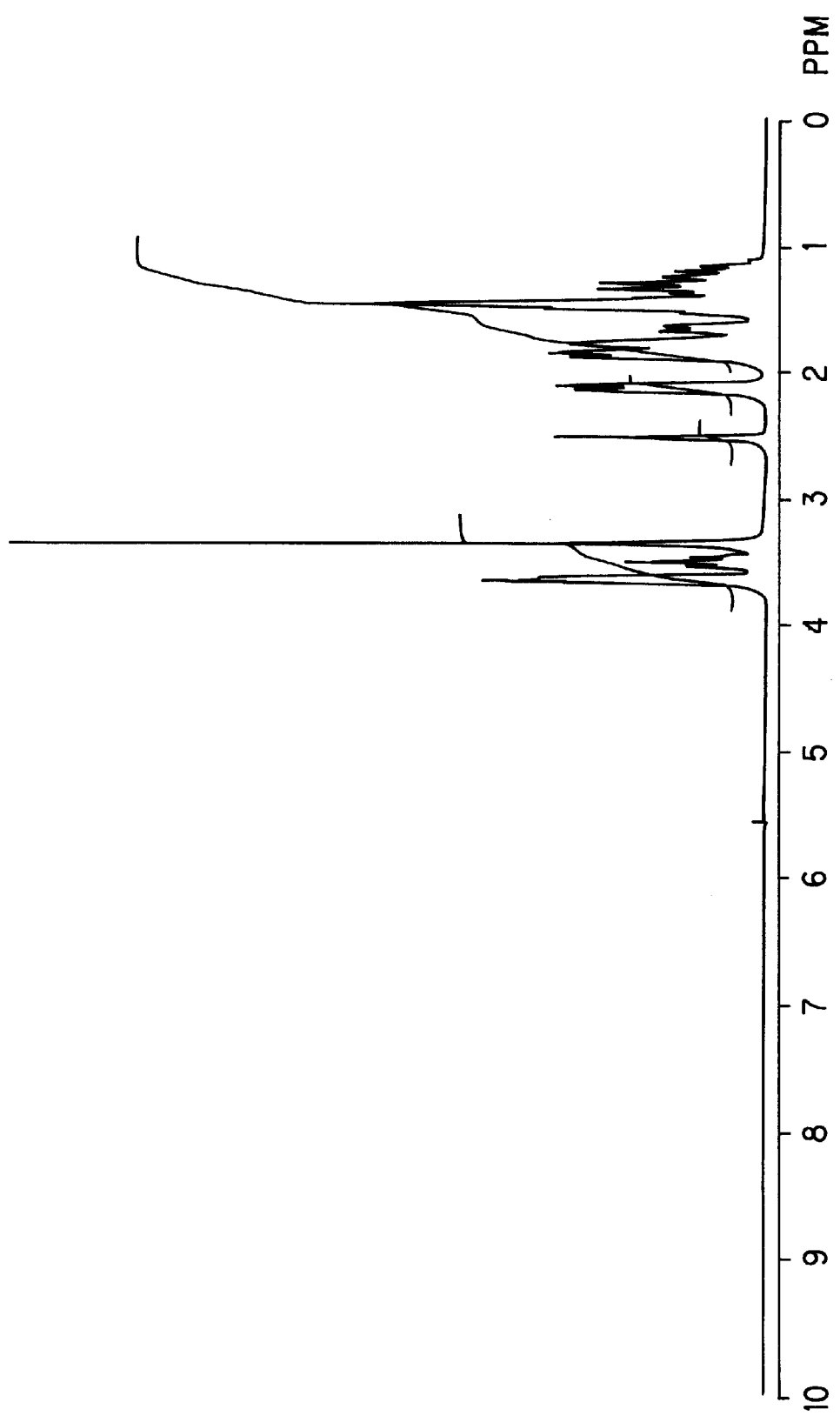
FIG. 9 is a proton NMR spectrum of 1,6-bis(cyclohexylsulfonyl diazomethylsulfonyl) hexane prepared in Example 5.
Figure 10:
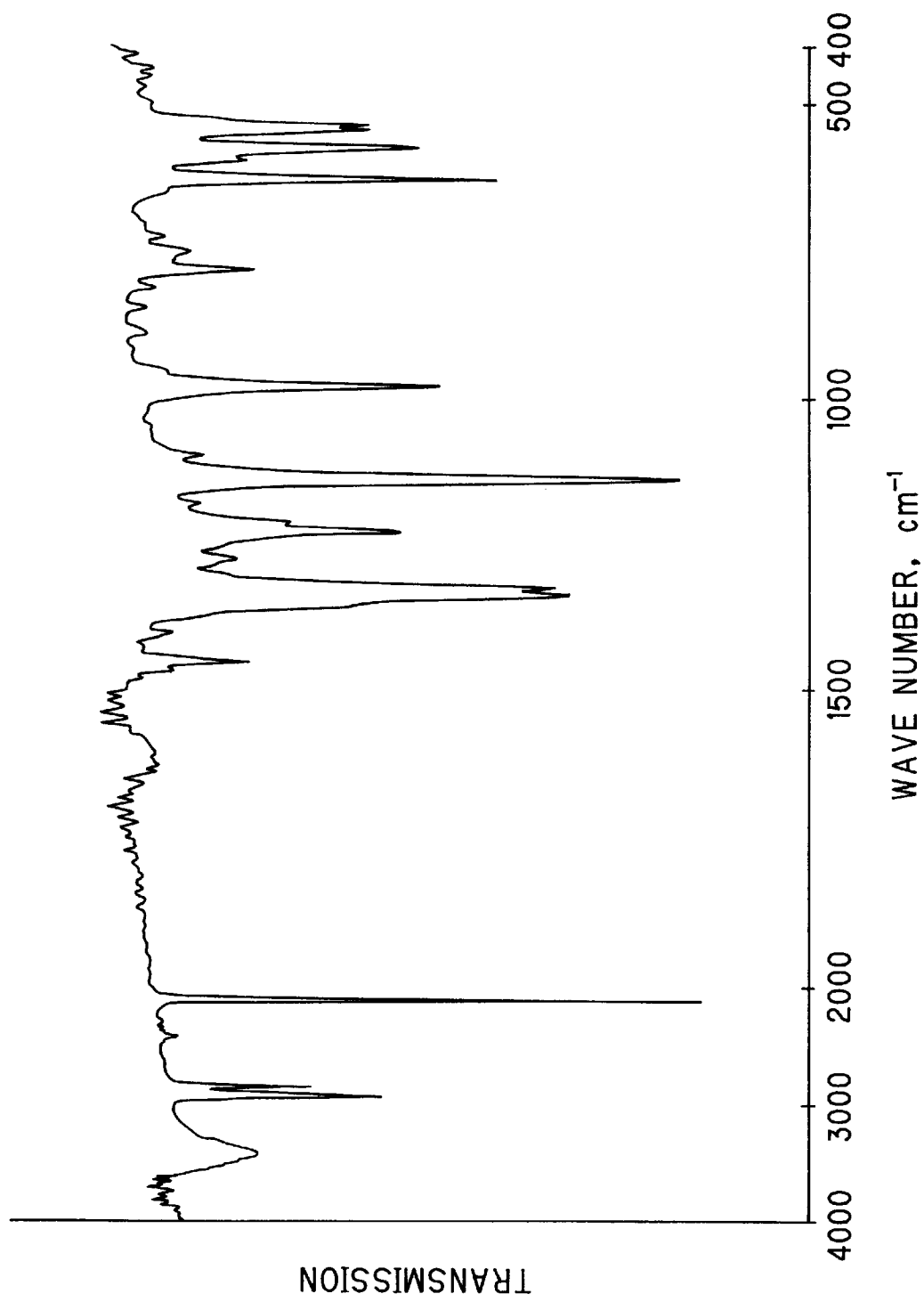
FIG. 10 is an infrared absorption spectrum of 1,6-bis(cyclohexylsulfonyl diazomethylsulfonyl) hexane prepared in Example 5.

FIG. 9 and FIG. 10 of the accompanying drawing show a proton NMR spectrum and an infrared absorption spectrum, respectively, of this compound.

EXAMPLE 6

A chemical-amplification positive-working photoresist composition in the form of a solution was prepared by dissolving, in 525 parts of propyleneglycol monomethyl ether acetate, 30 parts of a first polyhydroxystyrene resin having a weight-average molecular weight of 8000 with a molecular weight dispersion (weight-average molecular weight:number-average molecular weight=Mw:Mn) of 1.2, of which 30% of the hydroxyl groups were substituted for the hydrogen atoms by tetrahydropyranyl groups, 70 parts of a second polyhydroxystyrene resin having a weight-average molecular weight of 8000 with a molecular weight dispersion Mw:Mn of 1.2, of which 39% of the hydroxyl groups were substituted for the hydrogen atoms by 1-ethoxyethyl groups, 5.9 parts of the 1,6-bis(cyclohexylsulfonyl diazomethylsulfonyl) hexane prepared in Example 5, 0.12 part of tributylamine, 0.12 part of triisopropanolamine and 0.053 part of malonic acid followed by filtration of the solution through a membrane filter of 0.2 $\mu$m pore diameter.

Separately, a 6-inch semiconductor silicon wafer was provided on one surface with an organic antireflection coating film of 120 nm thickness by coating with a coating solution therefor (SWK-EX2, a product by Tokyo Ohka Kogyo Co.) followed by drying and a baking treatment at 200° C. for 90 seconds to give a substrate.

The substrate was coated on the antireflection coating film with the above prepared positive-working photoresist solution on a spinner followed by heating on a hot plate at 90° C. for 90 seconds to give a dried photoresist layer of 0.63 $\mu$m thickness.

The photoresist layer on the substrate was exposed pattern-wise to KrF excimer laser beams of 248 nm wavelength on a minifying projection exposure machine (Model FPA-3000EX3, manufactured by Canon Co.) and then subjected to a post-exposure baking treatment at 110° C. for 90 seconds followed by a puddle development treatment with a 2.38% by weight aqueous solution of tetramethylammonium hydroxide at 23° C. for 60 seconds, then rinsing in a running stream of pure water for 30 seconds and finally a post-development baking treatment at 100° C. for 60 seconds to give a positively patterned resist layer on the substrate surface.

The minimum exposure dose to obtain a line-and-space pattern of 0.25 $\mu$m line width as a measure of the photosensitivity was 61 mJ/cm$^2$ and the critical pattern resolution there was 0.17 $\mu$m. The patterned resist layer had a cross sectional profile close to orthogonal. A test patterning was undertaken for an isolated pattern to find that a resist pattern of 0.17 $\mu$m line width exhibited relatively small film thickness reduction with a cross sectional profile close to orthogonal.

COMPARATIVE EXAMPLE 1

A comparative photoresist solution was prepared in substantially the same formulation as in Example 6 excepting for the replacement of 5.9 parts of 1,6-bis (cyclohexylsulfonyl diazomethylsulfonyl) hexane as the acid-generating agent with 3.3 parts of bis (cyclohexylsulfonyl) diazomethane. The procedure of the test patterning was the same as in Example 6.

The minimum exposure dose to obtain a line-and-space pattern of 0.25 $\mu$m line width as a measure of the photosensitivity was 56 mJ/cm$^2$ and the critical pattern resolution there was 0.18 $\mu$m. The patterned resist layer had a cross sectional profile close to orthogonal. A test patterning was undertaken for an isolated pattern to find that the resist pattern of 0.17 μm width was inferior as compared with Example 6 in respect of film thickness reduction and the cross sectional profile at the same exposure dose.

COMPARATIVE EXAMPLE 2

A comparative photoresist solution was prepared in substantially the same formulation as in Example 6 excepting for the replacement of 5.9 parts of 1,6-bis (cyclohexylsulfonyl diazomethylsulfonyl) hexane as the acid-generating agent with 3.8 parts of bis(2,4-dimethylphenylsulfonyl) diazomethane. The procedure of the test patterning was the same as in Example 6.

The minimum exposure dose to obtain a line-and-space pattern of 0.25 μm line width as a measure of the photosensitivity was 20 mJ/cm$^2$ and the critical pattern resolution there was 0.18 μm. The patterned resist layer had a trapezoidal cross sectional profile close to triangular. A test patterning was undertaken for an isolated pattern to find that the resist pattern of 0.17 μm line width exhibited a large film thickness reduction and the cross sectional profile was poor at the same exposure dose.

COMPARATIVE EXAMPLE 3

A comparative photoresist solution was prepared in substantially the same formulation as in Example 6 excepting for the replacement of 5.9 parts of 1,6-bis (cyclohexylsulfonyl diazomethylsulfonyl) hexane as the acid-generating agent with 2.5 parts of bis(n-propylsulfonyl) diazomethane. The procedure of the test patterning was the same as in Example 6.

The minimum exposure dose to obtain a line-and-space pattern of 0.25 μm line width as a measure of the photosensitivity was 79 mJ/cm$^2$ and the critical pattern resolution there was 0.20 μm. The patterned resist layer had a trapezoidal cross sectional profile with a somewhat narrower top flat than the bottom. A test patterning was undertaken for an isolated pattern to find that the resist pattern of 0.18 μm width could hardly be formed.

EXAMPLE 7

A chemical-amplification positive-working photoresist composition in the form of a solution was prepared by dissolving, in 525 parts of propyleneglycol monomethyl ether acetate, 55 parts of a first polyhydroxystyrene resin having a weight-average molecular weight of 8000 with a molecular weight dispersion Mw:Mn of 4.0, of which 33% of the hydroxyl groups were substituted for the hydrogen atoms by 1-ethoxy-ethyl groups, 45 parts of a second polyhydroxystyrene resin having a weight-average molecular weight of 8000 with a molecular weight dispersion Mw:Mn of 4.0, of which 33% of the hydroxyl groups were substituted for the hydrogen atoms by tert-butoxycarbonyl groups, 3.2 parts of the 1,3-bis(phenylsulfonyl diazomethylsulfonyl) propane prepared in Example 1, 0.11 part of triethylamine, 0.60 part of salicylic acid and 2.3 parts of dimethyl acetamide followed by filtration of the solution through a membrane filter of 0.2 μm pore diameter.

A 6-inch semiconductor silicon wafer was coated with the above prepared positive-working photoresist solution on a spinner followed by heating on a hot plate at 90° C. for 90 seconds to give a dried photoresist layer of 0.74 μm thickness.

The photoresist layer on the substrate was exposed pattern-wise to KrF excimer laser beams of 248 nm wavelength on a minifying projection exposure machine (Model FPA-3000EX3, supra) and then subjected to a post-exposure baking treatment at 100° C. for 90 seconds followed by a puddle development treatment with a 2.38% by weight aqueous solution of tetramethylammonium hydroxide at 23° C. for 60 seconds, then rinsing in a running stream of pure water for 30 seconds and finally a post-development baking treatment at 100° C. for 60 seconds to give a positively patterned resist layer on the substrate surface.

The minimum exposure dose by which the photoresist layer in the exposed areas was completely dissolved away in the development treatment as a measure of the photosensitivity was 8 mJ/cm$^2$ and a line-and-space pattern of 0.20 μm line width had a good orthogonal cross sectional profile. The focusing depth latitude for obtaining a line-and-space pattern of 0.20 μm line width was 1.0 μm.

EXAMPLE 8

The experimental procedure was substantially the same as in Example 7 excepting for the replacement of the 1,3-bis (phenylsulfonyl diazomethylsulfonyl) propane prepared in Example 1 with the same amount of the 1,4-bis (phenylsulfonyl diazomethylsulfonyl) butane prepared in Example 2. The results of the evaluation tests were that the photosensitivity was 8 mJ/cm$^2$, the focusing depth latitude was 1.2 μm and the line-and-space pattern of 0.20 μm line width had an orthogonal cross sectional profile.

COMPARATIVE EXAMPLE 4

The experimental procedure was substantially the same as in Example 7 excepting for the replacement of 3.2 parts of the 1,3-bis(phenylsulfonyl diazomethylsulfonyl) propane prepared in Example 1 as the acid-generating agent with 2.3 parts of bis(2,4-dimethylphenylsulfonyl) diazomethane. The results of the evaluation tests were that the photosensitivity was 12 mJ/cm$^2$, the focusing depth latitude was 0.8 μm and the line-and-space pattern of 0.20 μm line width had an orthogonal cross sectional profile.

What is claimed is:

1. A poly(disulfonyl diazomethane) compound represented by the general formula

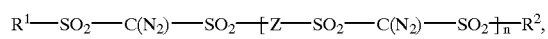

in which the subscript n is a positive integer not exceeding 5, R$^1$ and R$^2$ are each, independently from the other, a monovalent cyclic hydrocarbon group having 6 to 15 carbon atoms and Z is a divalent hydrocarbon group.

2. The poly(disulfonyl diazomethane) compound as claimed in claim 1 in which R$^1$ and R$^2$ are each, independently from the other, a cycloalkyl group, aryl group or aralkyl group.

3. The poly(disulfonyl diazomethane) compound as claimed in claim 2 in which R$^1$ and R$^2$ are each, independently from the other, a cyclohexyl group or a phenyl group.

4. The poly(disulfonyl diazomethane) compound as claimed in claim 1 in which Z is an alkylene group having 1 to 10 carbon atoms.

5. The poly(disulfonyl diazomethane) compound as claimed in claim 1 in which the subscript n is 1.

6. The poly(disulfonyl diazomethane) compound as claimed in claim 1 selected from the group consisting of:

1,3-bis(phenylsulfonyl diazomethylsulfonyl) propane,
1,4-bis(phenylsulfonyl diazomethylsulfonyl) butane,
1,6-bis(phenylsulfonyl diazomethylsulfonyl) hexane, 1,10-bis(phenylsulfonyl diazomethylsulfonyl) decane, 1,2-bis(cyclohexylsulfonyl diazomethylsulfonyl) ethane, 1,3-bis(cyclohexylsulfonyl diazomethylsulfonyl) propane, 1,6-bis(cyclohexylsulfonyl diazomethylsulfonyl) hexane and 1,10-bis(cyclohexylsulfonyl diazomethylsulfonyl) decane.

\* \* \* \* \*

UNITED STATES PATENT AND TRADEMARK OFFICE
CERTIFICATE OF CORRECTION

PATENT NO. : 6,153,733
DATED : November 28, 2000
INVENTOR(S) : Hiroto YUKAWA et al.

It is certified that error appears in the above-identified patent and that said Letters Patent is hereby corrected as shown below:

On the cover page, the title should read
--POLY(DISULFONYL DIAZOMETHANE) COMPOUND--.

Signed and Sealed this

First Day of May, 2001

Attest:

NICHOLAS P. GODICI

*Attesting Officer*      *Acting Director of the United States Patent and Trademark Office*